United States Patent [19]

Farley et al.

[11] Patent Number: 5,356,394
[45] Date of Patent: Oct. 18, 1994

[54] CANNULA WITH BALL VALVE

[76] Inventors: Kevin Farley, 4227 Susan Dr., Williamsville, N.Y. 14221; Daniel M. Gudeman, 526 Chesterfield Ln., Barrington, Ill. 60010

[21] Appl. No.: 959,221

[22] Filed: Oct. 9, 1992

[51] Int. Cl.5 .................................. A61M 5/00
[52] U.S. Cl. ............................. 604/256; 604/167; 604/246; 604/247; 604/249
[58] Field of Search ........... 604/27, 30, 33, 164–169, 604/246, 249, 247, 256, 283–284; 137/329.1–329.3, 901, 903; 251/149.6, 149.7

[56] References Cited

U.S. PATENT DOCUMENTS

| 60,082 | 11/1866 | Streett et al. | 137/901 |
|---|---|---|---|
| 1,034,995 | 8/1912 | Gannon | 137/901 |
| 3,192,949 | 7/1965 | De Gee | 137/903 |
| 3,399,677 | 9/1968 | Gould et al. | 137/903 |
| 4,036,210 | 7/1977 | Campbell et al. | |
| 4,072,291 | 2/1978 | Adams | 137/903 |
| 4,112,932 | 9/1978 | Chiulli | |
| 4,233,982 | 11/1980 | Bauer et al. | 604/169 |
| 4,240,411 | 12/1980 | Hosono | 128/4 |
| 4,245,635 | 1/1981 | Kontos | 604/169 |
| 4,261,357 | 4/1981 | Kontos | 604/169 |
| 4,510,933 | 4/1985 | Wendt et al. | 128/207.14 |
| 4,535,773 | 8/1985 | Yoon | |
| 4,601,710 | 7/1986 | Moll | 604/165 |
| 4,617,929 | 10/1986 | Gill | |
| 4,794,911 | 1/1989 | Okada | |
| 4,796,615 | 4/1989 | Bullock et al. | 604/283 |
| 4,917,668 | 4/1990 | Haindl | 604/167 |
| 4,943,280 | 6/1990 | Lander | 604/169 |
| 5,053,016 | 10/1991 | Lander | 604/169 |
| 5,057,084 | 10/1991 | Ensminger et al. | 604/167 |
| 5,098,394 | 3/1992 | Luther | 604/167 |
| 5,104,383 | 4/1992 | Shichman | 604/167 |
| 5,116,353 | 5/1992 | Green | |
| 5,125,915 | 6/1992 | Berry et al. | 604/283 |
| 5,131,429 | 7/1992 | Nixon | 251/149.7 |
| 5,141,498 | 8/1992 | Christan | 604/167 |
| 5,180,373 | 1/1993 | Green et al. | 604/167 |
| 5,180,376 | 1/1993 | Fischell | 604/159 |
| 5,197,955 | 3/1993 | Stephens et al. | 604/167 |
| 5,209,737 | 5/1993 | Richart et al. | 604/167 |
| 5,226,879 | 6/1993 | Ensminger et al. | 604/157 |
| 5,261,895 | 11/1993 | Kablik | 604/249 |

FOREIGN PATENT DOCUMENTS 3048203 7/1982 Fed. Rep. of Germany ........ 604/51
2267801 11/1975 France ................................. 604/249

Primary Examiner—C. Fred Rosenbaum
Assistant Examiner—Mark Bockelman
Attorney, Agent, or Firm—William J. Crossetta

[57] ABSTRACT

An improved cannula for providing access to a body passage for inserting instruments. The cannula of the present invention includes an improvement in the form of a biased ball valve for sealing the inlet of a housing attached to the proximal end of the cannula. The ball valve includes a seal member with an upwardly curved portion that is biased towards a second seal portion at a second end of the housing whereby the ball seats and seals the inlet to the housing cavity.

17 Claims, 6 Drawing Sheets

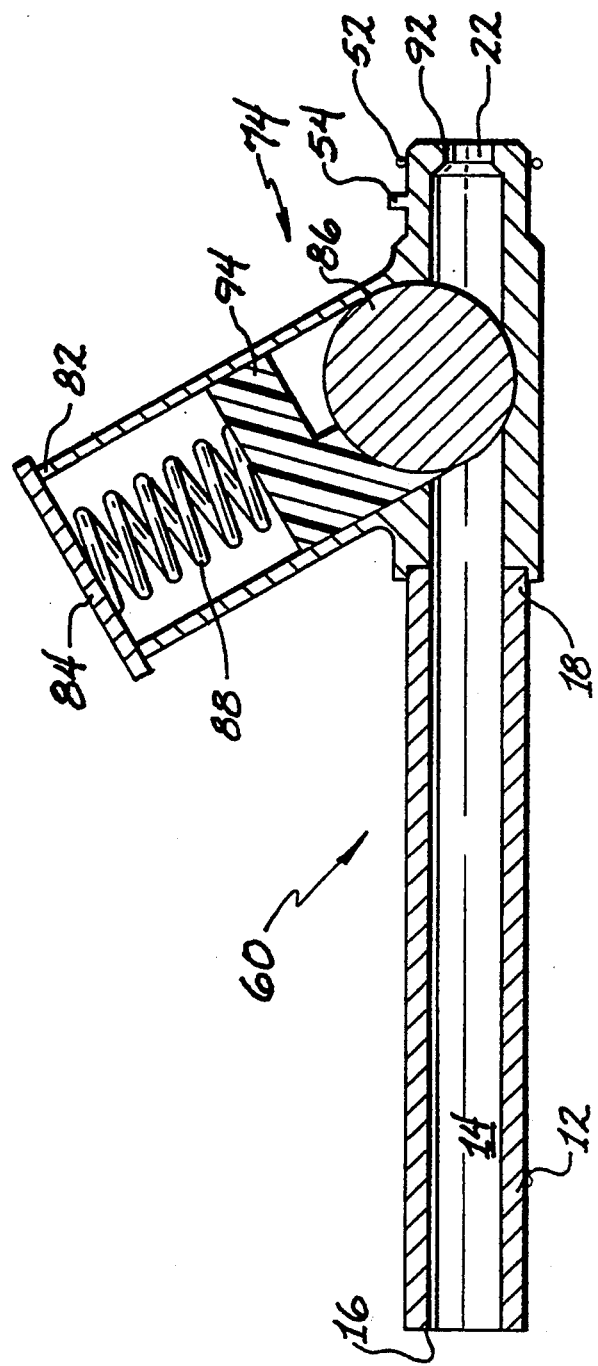

5,356,394

CANNULA WITH BALL VALVE

BACKGROUND OF THE INVENTION

1. Field of the Invention

This invention relates generally to a surgical cannula and more particularly to a cannula that utilizes a ball valve requiring no manual manipulation for its use.

2. Description of the Prior Art

Cannulas are hollow sleeves that are used to allow surgical instruments to be introduced into a body cavity. First, the cannula with trocar is introduced into the body (the trocar is removed) and then the surgical instruments are placed through the cannula into the body. Often, when surgery is being performed a gas is entering into the body cavity targeted for surgery so that there is room for surgical instruments to be manipulated within the cavity. Therefore, it is important that the cannula through which the surgical instruments are entered into the body cavity do not allow this gas to exit the body cavity.

It is known in the industry to use cannulas having trumpet valves incorporated therein. The trumpet valves must be manually manipulated during insertion and removal of the surgical instruments so that a seal preventing the release of gas is maintained in the cannula. The trumpet valves which must clamp around the instruments can be traumatic to the instruments themselves. Furthermore, the requirement of manual manipulation of the trumpet valve is cumbersome and inhibits focused attention being given to the manipulation of the surgical instruments themselves.

SUMMARY OF THE INVENTION

We provide a cannula having an elongated hollow cannula body. The cannula body defines a cannula passage running therethrough. The cannula passage is sized so as to accommodate instruments such as surgical instruments disposed therethrough. The cannula body has a distal end that is to be disposed within the human body and also has a proximal end located opposite to the distal end. A ball valve is connected to the cannula body proximal end. The ball valve has a hollow valve housing defining a cavity therein. Located at opposite sides of the valve housing are an inlet opening and an outlet opening. The inlet and outlet and the portion of the valve housing cavity lying between them are sized to accommodate instruments disposed therethrough. The valve housing further has a first end and a second end located at opposite ends of the housing. Preferably, the first and second ends have closures secured thereon which may be part of the valve housing or may be a separate structure attached to the valve housing.

The valve is connected to the cannula body by connecting the valve outlet to the cannula body proximal end such that the cannula passage and a portion of the valve cavity between the inlet and the outlet are connected and colinear. The valve also has a movable ball disposed within the valve cavity between the first end and the second end. The ball may be made of any suitable material but is preferably made of a lightweight material such as nylon. A means for biasing the valve toward a sealed position is also provided. In the sealed position the moveable ball is situated between the valve inlet and the valve outlet in engagement with the interior of the valve housing surrounding the inlet and outlet such that fluids are prevented from passing between the valve inlet and the outlet.

It is preferred that a first sealing portion and a second sealing portion are provided within the valve cavity so as to enhance the sealing action of the valve when the valve is biased into a sealed position. The first sealing portion is slidably disposed within the valve cavity between the ball and the first end closure. The second sealing portion is disposed within the valve cavity between the ball and the second end closure. The first and second sealing portions are sized and configured so as to be in close engagement with the interior surface of the valve housing. Thus, when the first and second sealing portions are utilized in the valve, the first and second sealing portions and the ball cooperate to seal the valve so that fluids are prevented from traveling between the valve inlet and the valve outlet.

An opening to the valve is provided either at the valve inlet or on an end barrel attachment affixed to the inlet. The opening to the valve is sized to receive the surgical instruments. The opening is preferably sized and made of a suitable deformable material such that the opening is sealed upon insertion of the instrument.

In operation, the cannula distal end is inserted into a body cavity. When no instruments are disposed in the cannula, the biasing means places the cannula valve into a sealed position in which fluids cannot enter or exit the body cavity via the cannula. When it is desired to dispose instruments into the cannula, the instruments are inserted through the valve inlet. Once the instrument has entered the valve inlet, the inlet is sealed so that other material may not pass through the inlet. Upon further insertion into the cannula, the instrument contacts the movable ball. The traveling instrument causes the ball to overcome the biasing means and to travel within the valve cavity towards the valve housing first end. As the ball travels towards the first end, the obstructing ball between the inlet and the outlet is removed, thus placing the valve in an open position in which material may travel between the inlet and the outlet. When the valve is open removed, the instrument may pass through the valve outlet and through the cannula passage within the cannula body towards the distal end of the cannula body. Upon removal of the instrument, once the instrument has passed the ball the biasing means forces the ball between the inlet and the outlet placing the valve in a sealed position. The instrument can then safely be removed completely from the cannula without the escape of fluids through the cannula.

Other objects and advantages of the invention will become apparent from a description of certain present preferred embodiments thereof shown in the drawings.

BRIEF DESCRIPTION OF THE DRAWINGS

FIG. 4 is a side view taken in cross section of a second preferred embodiment of the cannula.

DESCRIPTION OF THE PREFERRED EMBODIMENT

Figure 1:
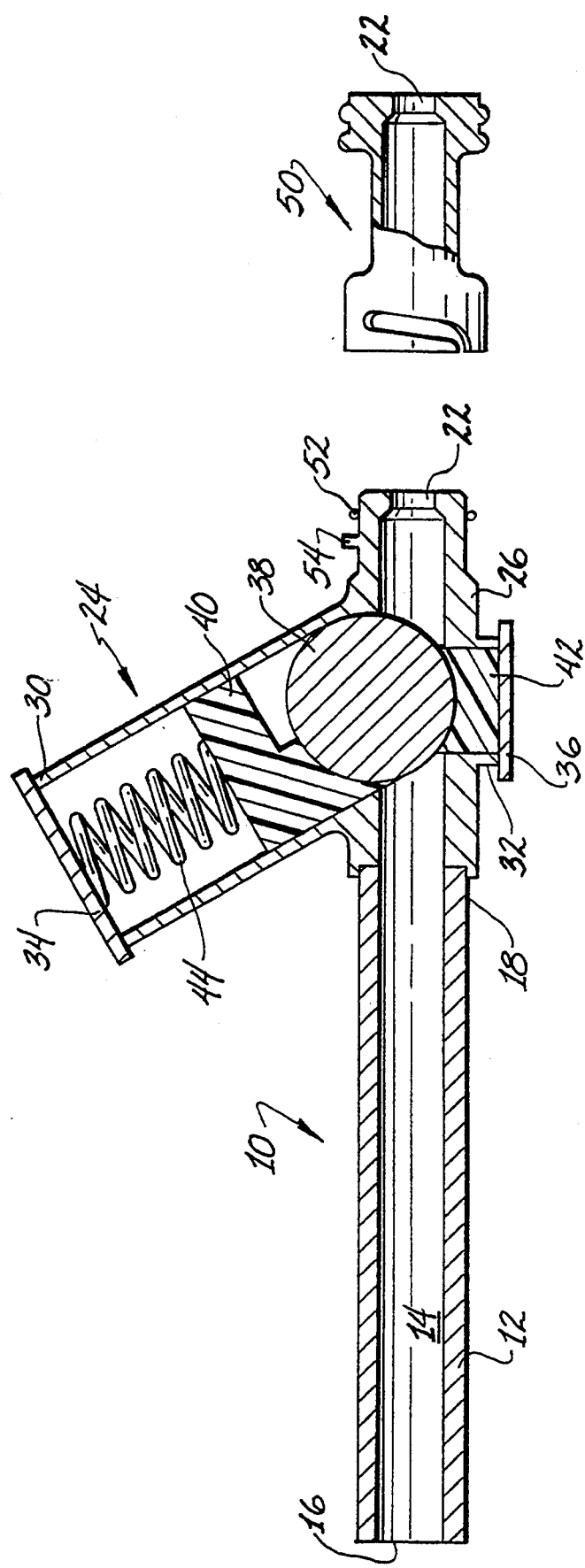
FIG. 1 is a side view taken in cross section of a first preferred embodiment of the cannula with its end barrel removed.
Figure 3:
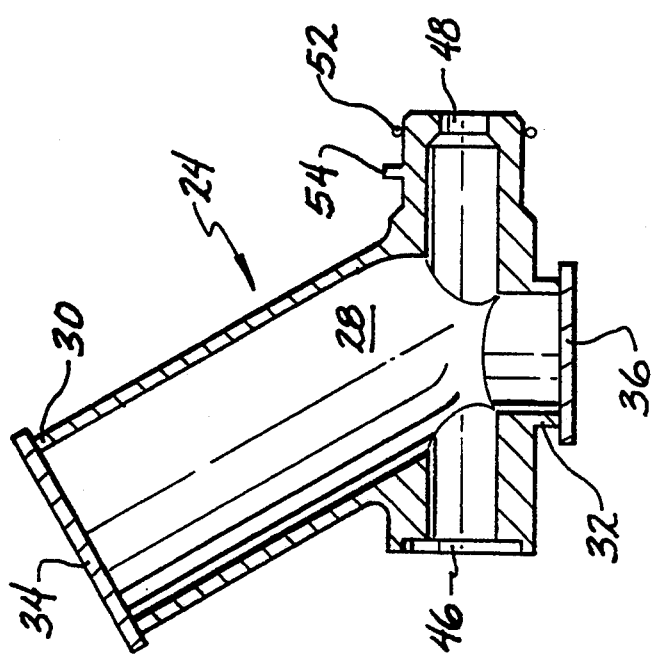
FIG. 3 is a side view taken in cross section of the preferred valve housing.

Referring first to FIGS. 1 and 3, a cannula 10 having a hollow cannula body 12 is shown. The cannula body 12 defines a cannula passage 14 running therethrough. The cannula passage 14 is sized so as to accommodate instruments (not shown) such as surgical instruments disposed therethrough. The cannula body 12 has a distal end 16 that is to be disposed within a human body. The cannula body 12 also has a proximal end 18 located opposite to the distal end 16.

The cannula 10 also has a ball valve 24 connected to the cannula body proximal end 18. The ball valve 24 has a hollow valve housing 26 defining a cavity 28 therein. The valve housing 26 has an inlet 48 and an outlet 46 located at opposite sides of the housing 26. The inlet 48 and outlet 46 are openings sized to accommodate instruments disposed therethrough. The valve housing 26 further has a first end 30 and a second end 32 located at opposite ends of the housing 26. The first and second ends 30 and 32 have closures 34 and 36 affixed thereto. The valve 24 is connected to the cannula body 12 by connecting the valve outlet 46 to the cannula body proximal end 18 such that the cannula passage 14 and a portion of the valve cavity 28 between the inlet 48 and the outlet 46 are connected and colinear. The valve 24 also has a movable ball 38 disposed within the valve cavity 28 between the first end 30 and the second end 32. The ball 38 may be made of any suitable material but is preferably made of a lightweight material such as nylon. A means 44 for biasing the valve 24 into a sealed position is provided in which in the sealed position fluids are prevented from passing between the valve inlet 48 and the valve outlet 46.

It is preferred that a first and a second sealing portion 40 and 42 are provided within the valve cavity 28 so as to enhance the sealing action of the valve 24 when the valve 24 is biased into a sealed position. The first sealing portion 40 is slidably disposed within the valve cavity 28 between the ball 38 and the first end closure 34. The second sealing portion 42 is disposed within the valve cavity 28 between the ball 38 and the second end closure 36. The first and second sealing portions 40 and 42 are sized and configured so as to be in close engagement with the interior surface of the valve housing 26. Thus, when the first and second sealing portions 40 and 42 are utilized in the valve 24, the first and second sealing portions 40 and 42 and the ball 38 cooperate to seal the valve 24 so that fluids are prevented from traveling between the valve inlet 48 and the valve outlet 46. An opening 22 to the valve 24 is provided either at the valve inlet 48 or on an end barrel attachment 50 affixed to the inlet 48 which is sized to receive the surgical instruments. A sealing means, such as an O-ring (now shown), is provided at the opening 22 so that the opening 22 will be sealed upon insertion of the instruments. An optional reducer sleeve (now shown) may also be used.

In operation, the cannula distal end 16 is inserted into a body cavity. When no instruments are disposed in the cannula, the biasing means 44 places the cannula valve 24 into a sealed position shown in FIG. 1, in which fluids cannot enter or exit the body via the cannula. In the sealed position, the ball 38 lies between the valve inlet 48 and the valve outlet 46 so that material may not pass between the valve inlet and the valve outlet.

Figure 2:
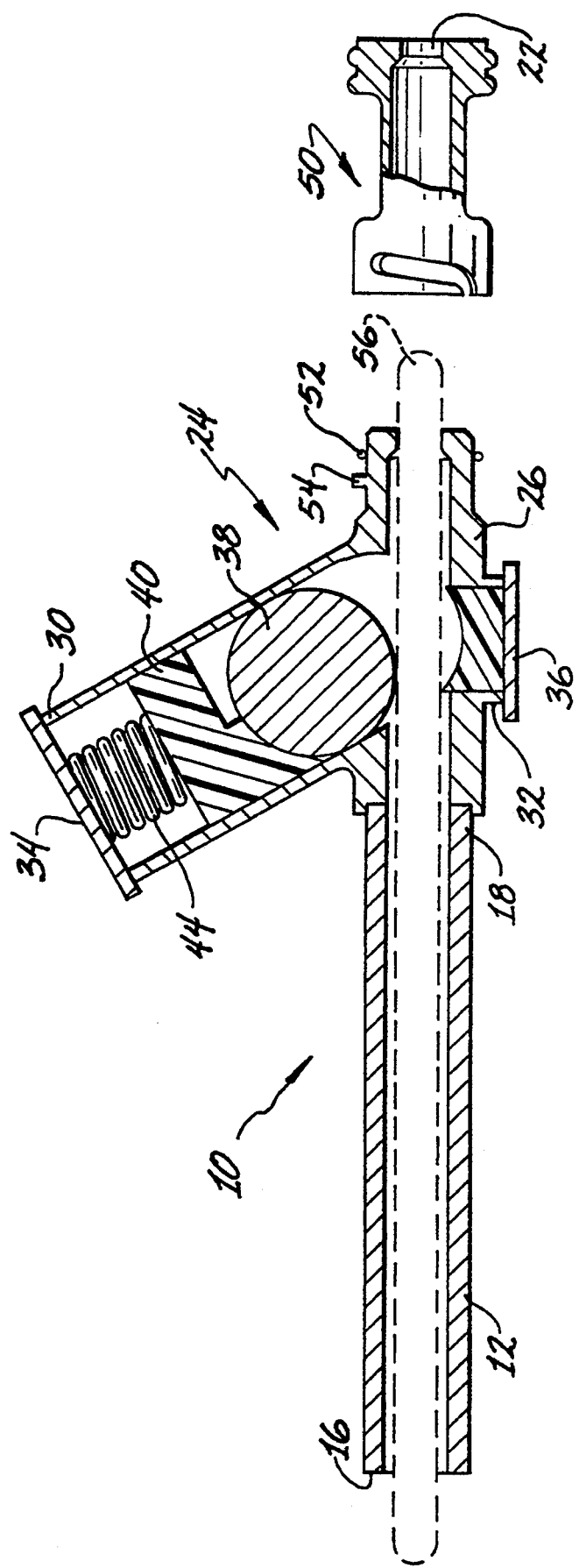
FIG. 2 is view similar to FIG. 1 in which the cannula valve is in an open position.

Referring next to FIGS. 2 and 3, when it is desired to dispose instruments into the cannula, an instrument 56 (shown in dotted Line in FIG. 2) is inserted through an opening 22 in the valve inlet 48. Once the instrument has entered the valve inlet 48, the inlet 48 is sealed so that other material may not pass through the inlet. Upon further insertion into the cannula, the instrument contacts the movable ball 38. The instrument causes the ball 38 to overcome the biasing means 44 and to travel within the valve cavity 28 towards the valve housing first end 30. As the ball 38 travels towards the first end 30, the obstruction between the inlet 48 and the outlet 46 is removed, thus placing the valve 24 in an open position in which material may travel between the inlet 48 and the outlet 46. With the obstruction removed, material, including the instrument, are allowed to pass through the valve outlet 46 and through the cannula passage 14 within the cannula body 12 towards the distal end 16 of the cannula body.

Once the instrument has passed the ball during removal of the instrument, the biasing means 44 forces the ball 38 between the inlet 48 and the outlet 46 placing the valve 24 in a sealed position. The instrument can then safely be removed completely from the cannula without the escape of fluids through the cannula 10.

Figure 5:
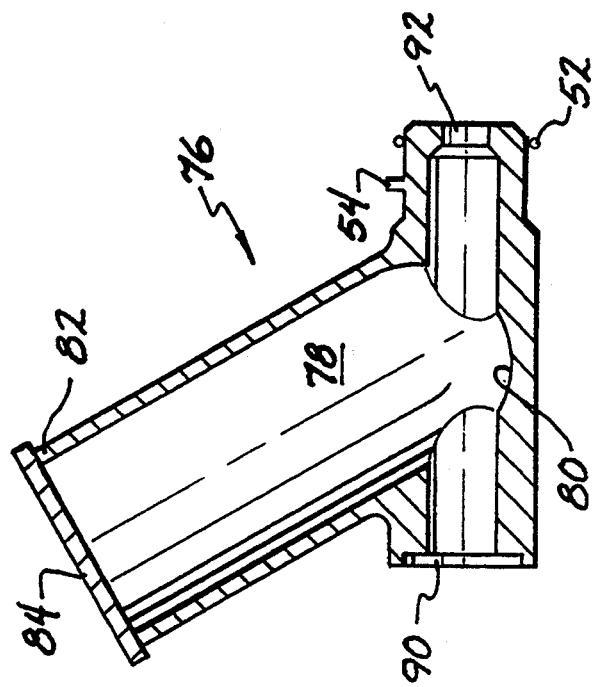
FIG. 5 is a side view taken in cross section of a second preferred valve housing.

Referring next to FIGS. 4 and 5, a second preferred embodiment of the cannula is shown. The second preferred embodiment of the cannula operates substantially identically to the first preferred embodiment and is structurally similar to the first preferred embodiment except for a second preferred ball valve 74. The valve 74 has a hollow valve housing 76 that defines a cavity 78 therein. The valve housing 76 has an inlet 92 and and outlet 90 located at opposite sides of the housing 76. The inlet 92 and outlet 90 are openings sized to accommodate instruments disposed therethrough. The valve housing 76 has a seat 80 and has an end 82 at an opposite end of the housing from the seat 80. The opposed end 82 has a closure 84 affixed thereto. The valve 74 is connected to the cannula body 12 by connecting the valve outlet 90 to the cannula body proximal end 18 such that the cannula passage 14 and a portion of the valve cavity 78 between the inlet 92 and the outlet 90 are connected and colinear. The valve 74 also has a movable ball 86 disposed within the valve cavity 78 between the valve seat 80 and the opposed end 82. The ball 86 may be made of any suitable material but is preferably made of a lightweight material such as nylon. When the ball 86 is pressed into engagement with the valve seat 80, fluids are prevented from passing between the valve inlet 92 and the valve outlet 90 and the valve 74 is said to be in a sealed position. A means 88 for biasing the ball 86 into the valve seat 80 is provided which is preferably a spring or other spring like components such as a section of the elastomeric material.

A sealing portion 94 may be slidably disposed within the valve cavity 78 between the ball 86 and the opposed end closure 84. The sealing portion 94 is sized and configured so as to be in close engagement with the interior surface of the valve housing 76. An opening 22 to the valve 74 is provided either at the valve inlet 92 or on the end barrel attachment 50 affixed to the inlet 92 which is sized to receive the surgical instruments. The opening 22 is preferably sized and the structure surrounding the opening 22 made of a suitable deformable material such that the opening 22 is sealed upon insertion of the instruments.

Figure 7:
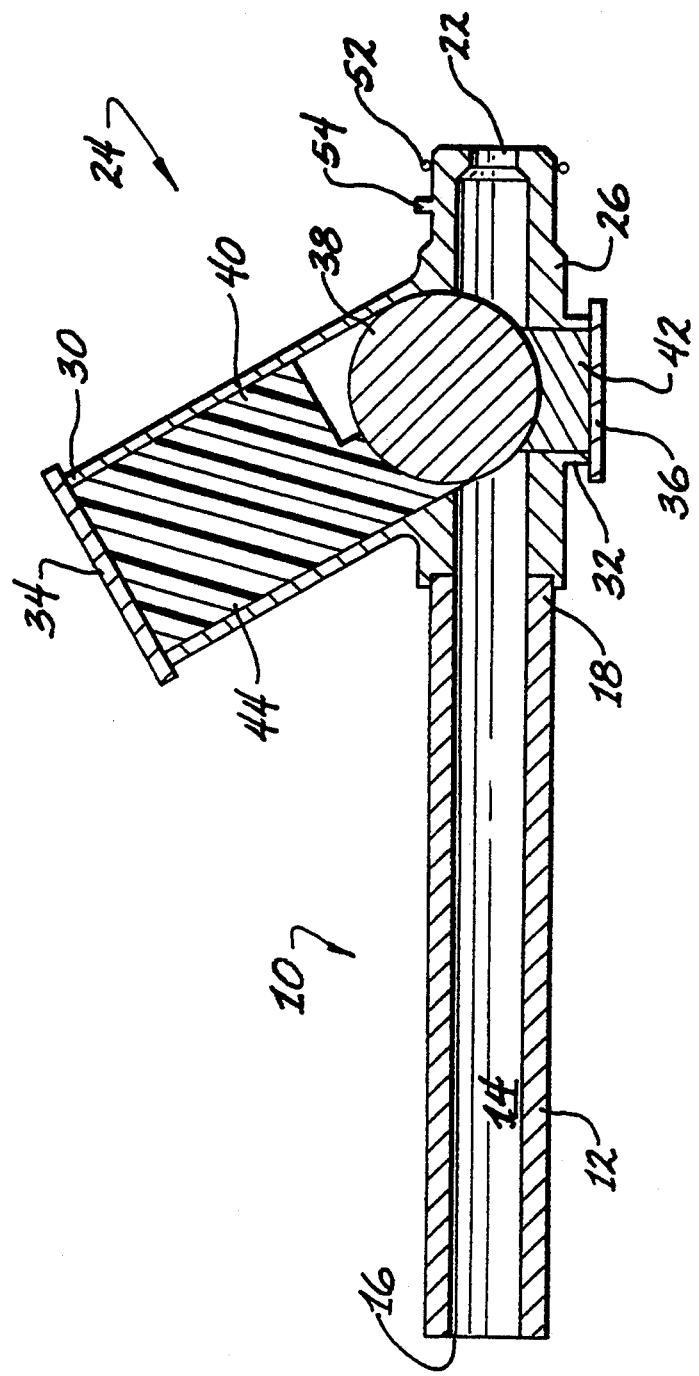
FIG. 7 is a side view taken in cross section of a third preferred embodiment of the cannula.

It is preferred that the first sealing portion 40, the second sealing portion 42 and the sealing portion 94 be fabricated of a nonporous elastomeric material such that the sealing portions being in tight engagement with the valve cavity provides a seal through which fluids may not pass. A third preferred embodiment shown in FIG. 7 utilizes a sealing portion between the first and closure and the ball, in which the sealing portion also acts as the biasing means. The sealing portion is made of an elastomeric material and extends completely from the first and closure in the ball. When an instrument enters the cannula, the ball is forced towards the first end of the valve housing, compressing the sealing portion. Once the instrument is removed from the cannula passage, the elastic nature of the sealing portion moves the ball back to the sealing position.

Variations of the preferred embodiments could be made. For example, it is understood that the first end closure 34, the second end closure 36 and the opposed end closure 84 may be part of the valve housing structure or may be a separate component affixed to the valve housing. Also, although the movable ball is preferably made of nylon, the ball can be made of any suitable material and may also be fabricated of a material that exhibits a certain amount of deformation such that the ball may conform somewhat within the valve cavity to better seal the valve.

Figure 6:
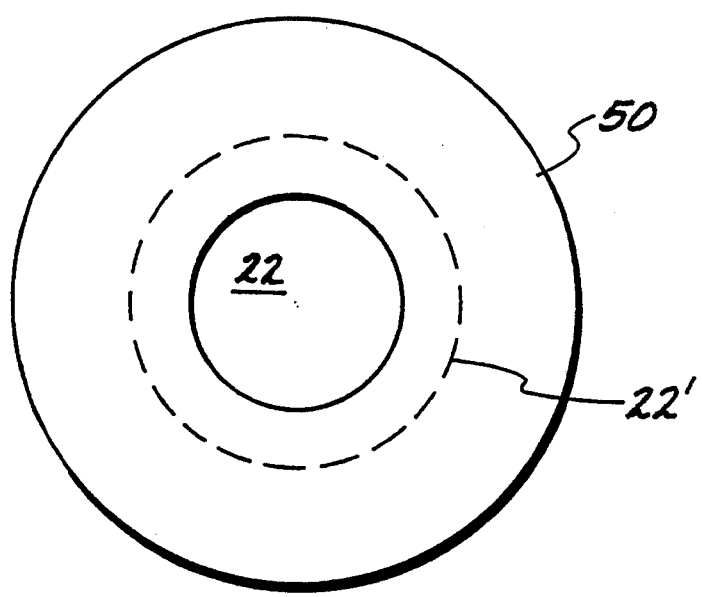
FIG. 6 is an end view of a preferred end barrel for the cannula.

Referring to FIGS. 1 and 6, it is also preferred that the end barrel 50 be capable of being selectively attached and detached from the valve inlet. Thus, end barrels of ranging configurations may be placed on the valve inlet. Particularly the end barrels may have different sized openings 22 placed at their end. A different sized opening 22' is shown by the dotted line in FIG. 6. This allows for a cannula that can accommodate various sized instruments while using the same valve and achieving a seal with different sized instruments. The end barrel and the valve are preferably sealed upon connection by an O-ring 52 or other appropriate seal. The preferred connection means is by equipping the cannula with a lock pin 54 that engages a slot (now shown) on the end barrel.

The valve housing first end preferably extends outward from the cannula body so that an angle of 30° is formed between the valve housing and the cannula body. This angle allows the ball to be more easily moved by the inserted instrument in that the force applied on the ball by the instrument is more nearly aligned to overcome the force applied by the biasing means than if the valve first end extended perpendicular to the cannula body. The cannula passage 14 has a center line shown in dotted line in FIG. 1 along a longitudinal axis of the cannula body. The ball has a center point which is located above the center line of the cannula body. Thus, as the instrument is inserted the ball is caused by contact with the instrument to be forced up the valve cavity towards the first end. The ball is able to roll along the instrument as the instrument is being inserted thereby providing a minimum resistance to insertion of the instrument.

The shape of the cannula passage is preferably cylindrical but may be any configuration that can accommodate the instrument. The valve opening 22 is preferably circular.

Additionally, the spring is preferably mounted to the first sealing portion at a point other than the center of the first sealing portion to provide a better seal. The amount of surface area contact between the sealing portions and the ball is minimized so as to allow the ball to rotate more freely.

While certain present preferred embodiments have been shown and described, it is distinctly understood that the invention is not limited thereto but may be otherwise embodied within the scope of the following claims.

We claim:

1. An improved cannula having a hollow body defining a cannula passage sized to receive instruments running therethrough, the cannula body having a distal end to be disposed in the human body and having a proximal end, wherein the improvement comprises a ball valve connected to the proximal end of said cannula body, the valve comprising:
    (a) a hollow valve housing defining a cavity, the valve housing having an inlet and an outlet to said cavity sized to receive instruments, the inlet and outlet being located at opposite sides of the housing and being arranged along a first axis collinear with said cannula passage, the cavity further having a first end and a second end located opposite thereto, said ends being arranged along a second axis which intersects said first axis, the outlet being connected to the proximal end of the cannula body such that the cannula passage and a portion of the valve cavity between the inlet and the outlet are connected and collinear;
    (b) a movable ball disposed within the valve cavity between the first end and the second end along said second axis which intersects; and
    (c) first sealing means having upwardly curved face portion for engaging a portion of said ball and for pushing the ball along said second axis into an inlet sealing position, said seal means having associated therewith, biasing means for biasing the sealing means along said second axis.

2. The cannula of claim 1 wherein said housing comprises a first opening to said first end of said cavity and a second opening to said second end of said cavity, said first and second openings having means for closure.

3. The cannula of claim 2 wherein at least one of said first end closure and second end closure means is detachably fixed to said housing.

4. The cannula of claim 3 wherein at least one of said first end closure means and second end closure means are made of the same material as the valve housing.

5. The cannula of claim 1 further comprising said first sealing means slidably disposed within the valve cavity between the ball and the valve housing first end, the first sealing means being in bias cooperating close engagement with the interior surface of the valve housing.

6. The cannula of claim 5 further comprising a second sealing portion disposed within the valve cavity between the ball and the second end, the second sealing portion being in close engagement with the interior surface of the valve housing in which the means for biasing the ball from an open position to a sealed position biases said first sealing means towards the ball and biases the ball towards the second sealing portion, the first and second sealing portions cooperating to prevent fluids from passing between the valve inlet and valve outlet.

7. The cannula of claim 6 wherein the first sealing means and the second sealing portion are made of an elastomeric material.

8. The cannula of claim 7 wherein the means for biasing said first sealing means and said ball from an open position to a sealed position is the first sealing means extending from the ball to the first end.

9. The cannula of claim 5 wherein the valve housing first end extends outward from the cannula body at an angle of 30°.

10. The cannula of claim 1 wherein the inlet is sized for receiving instruments such that the inlet is sealed upon insertion of the instrument.

11. The cannula of claim 1 wherein the means for biasing said first sealing means and said ball from an open position to a sealed position is a spring disposed between the valve housing first end and said first sealing means and said ball.

12. The cannula of claim 1 further comprising an end barrel affixed to the inlet of the valve, the end barrel having an opening for receiving instruments, the end barrel opening being sized such that the opening is sealed upon insertion of the instrument.

13. The cannula of claim 12 wherein the end barrel is detachably affixed to the inlet of the-valve such that a number of end barrels having different sized openings may be affixed thereto.

14. The cannula of claim 1 wherein the ball is made of nylon.

15. The cannula of claim 1 wherein the ball is made of an elastomeric material.

16. The cannula of claim 1 wherein said first axis comprises a centerline collinear with a centerline of the cannula passage and the center of the ball is located above the center line of said axis.

17. The cannula of claim 3 wherein the means for biasing said first sealing means and said ball from an open position to a sealed position biases the ball toward the sealed position.

* * * * *